United States Patent [19]

Nelson

[11] Patent Number: 4,908,466
[45] Date of Patent: Mar. 13, 1990

[54] PROCESS AND REACTION VESSEL FOR PRODUCTION OF ALKYL NITRITE

[75] Inventor: James R. Nelson, South Charleston, W. Va.

[73] Assignee: Union Carbide Chemicals and Plastics Company Inc., Danbury, Conn.

[21] Appl. No.: 102,367

[22] Filed: Sep. 29, 1987

[51] Int. Cl.$^4$ ............................................. C07C 76/04
[52] U.S. Cl. .................................................... 558/488
[58] Field of Search ........................................ 558/488

[56] References Cited

U.S. PATENT DOCUMENTS

| | | | |
|---|---|---|---|
| 2,166,698 | 7/1939 | Allen | 558/488 |
| 2,465,984 | 3/1949 | Doumani et al. | 558/488 |
| 2,739,166 | 3/1956 | Treacy | 558/488 |
| 2,831,882 | 4/1958 | Spaeth | 558/488 |
| 2,977,384 | 3/1961 | Bentley et al. | 558/488 |
| 4,353,843 | 10/1982 | Doumaux et al. | 260/466 |
| 4,629,806 | 12/1986 | Cleveland et al. | 560/204 |

Primary Examiner—John F. Terapane
Assistant Examiner—Valerie D. Fee
Attorney, Agent, or Firm—Morris N. Reinisch

[57] ABSTRACT

A process and reaction vessel for producing alkyl nitrite is disclosed the process comprising (a) contacting nitric oxide, lower alcohol and oxygen in a reaction zone such that alkyl nitrite is formed, said reaction zone comprising a reactor section and a rectification section, (b) supplying a liquid scrubbing agent to an upper portion of the rectification section, (c) withdrawing a gaseous alkyl nitrite product stream from the upper portion of the rectification section, and (d) withdrawing a liquid stream from a lower portion of the reactor section. The reactor section provides intimate vapor-liquid contact sufficient to enhance the conversion of nitric oxide to alkyl nitrite and the rectification section provides sufficient vapor residence time to enhance conversion of oxygen, as well as sufficient rectification capabilities to reduce the amounts of water and nitric acid in the gaseous alkyl nitrite product stream.

8 Claims, 2 Drawing Sheets

PROCESS AND REACTION VESSEL FOR PRODUCTION OF ALKYL NITRITE

BACKGROUND OF THE INVENTION

1. Field of the Invention

The subject invention is directed to a process for preparing alkyl nitrites, particularly methyl nitrite, and a reaction vessel for carrying out the process.

2. Description of Related Art

Alkyl nitrites, i.e., esters of nitrous acid, have been found useful in a variety of areas including additives to motor fuels, stabilizers for vinyl compounds such as spasmolytic agents, reagents for diazotization and reagents for chemical synthesis. Processes for preparing alkyl nitrites can be found, inter alia, in U.S. Pat. Nos. 4,229,591; 4,353,843 and 4,629,806 and in Japanese Application No. 53-8268. The process for forming alkyl nitrites (referred to herein as the nitrite process) may be understood more fully by reference to the following equations:

(1) $2NO + O_2 \rightarrow 2NO_2$ (2) $NO_2 + NO \rightleftharpoons N_2O_3$ (3) $ROH + N_2O_3 \rightarrow RONO + HONO$ (4) $ROH + HONO \rightarrow RONO + H_2O$ (5) $N_2O_3 + H_2O \rightarrow 2HONO$ (6) $2NO_2 \rightleftharpoons N_2O_4$ (7) $ROH + N_2O_4 \rightarrow RONO + HNO_3$ (8) $N_2O_4 + H_2O \rightarrow HONO + HNO_3$ wherein R represents a methyl or ethyl group.

The desired reaction sequence for the formation of alkyl nitrite occurs via Reactions (1)–(4). The sum of these reactions yields as the overall process reaction:

(I) $2ROH + 2NO + 1/2 O_2 \rightarrow 2RONO + H_2O$

Reaction (5) takes place because the water formed in Reaction (4) can react with dinitrogen trioxide ($N_2O_3$). Reaction (5) can be tolerated provided enough alcohol is supplied to react with substantially all of the nitrous acid formed in Reaction (5) according to Reaction (4) yielding alkyl nitrite and additional water.

Reactions (6) through (8) are undesired since they lead to the formation of nitric acid, a compound which subsequently must be separated from product alkyl nitrite. Further, these reactions consume nitric oxide in forming undesired nitric acid. In order to reduce production of dinitrogen tetroxide ($N_2O_4$), via Reaction (6), the gas phase concentration of $NO_2$ should be minimized relative to that of NO. In this way, $N_2O_3$ is preferentially formed instead of $N_2O_4$. A relatively high NO to $NO_2$ ratio can be maintained by initially supplying a molar excess of NO relative to $O_2$, as indicated by the stoichiometry of Reaction (I), i.e., greater than 4 moles NO per mole $O_2$. In other words, to enhance production of alkyl nitrites such as methyl nitrite or ethyl nitrite, it generally is preferable to provide NO in a molar excess, preferably in such an amount that substantially all $O_2$ is consumed.

Vapor state formation of alkyl nitrite (nitrite process) by the general procedure described above preferably is coupled and correlated with vapor state formation of dialkyl oxalate from alkyl nitrite and carbon monoxide (oxalate process) in an integrated production cycle so as to provide an overall vapor state process (nitrite-oxalate process) that is cyclic in operation, e.g., see U.S. Pat. No. 4,629,806. Such a process is advantageous with regard to limiting the formation of by-products, ease of operation and production efficiency. Vapor state formation of dialkyl oxalate is conducted by contacting carbon monoxide and alkyl nitrite in a carbonylation reaction zone in the presence of a solid catalyst. The main reaction is illustrated by the following equation:

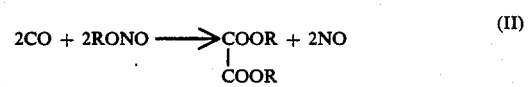

wherein R represents a methyl or ethyl group.

Preparation of dialkyl oxalates is of particular interest to the chemical industry because of the varied uses of these compounds. These diesters may serve as starting materials for the preparation of alkylene glycols such as ethylene glycol, a valuable commercial chemical which finds application in deicing fluids, antifreeze, hydraulic fluids and in the manufacture of alkyd resins, solvents, and polyester fibers. These diesters also are useful as intermediates in preparing dyes, pharmaceuticals, and the like.

As evident from the equation representing Reaction (II), for every mole of alkyl nitrite consumed, a mole of nitric oxide is generated. Nitric oxide thus formed may be recycled and used as a starting material for forming alkyl nitrites according to Reaction (I), thus completing the nitrite-oxalate reaction cycle. Dialkyl oxalate produced in the carbonylation reaction zone can be purified and recovered as product or further reacted, for example, by contacting it with hydrogen in a hydrogenation reaction zone to produce ethylene glycol.

To provide an efficient process for preparing alkyl nitrites, a number of performance criteria must be considered and satisfied.

First, oxygen conversion preferably should be as close to 100 percent as is possible (i.e., the amount of oxygen exiting the alkyl nitrite reactor preferably is minimized) without significantly adversely affecting other reactor performance characteristics. It also is preferred that substantially all higher nitrogen oxides, i.e., oxides of nitrogen other than nitric oxide, be consumed in the alkyl nitrite reactor.

Second, the efficiency of converting nitric oxide to alkyl nitrite, i.e., the percentage of nitric oxide converted to alkyl nitrite, the desired product, is maximized in the alkyl nitrite reactor while formation of undesired products such as nitric acid is minimized.

It also is preferred that substantially all water and nitric acid produced in the alkyl nitrite reactor be removed in a liquid tails stream by providing a scrubbing agent which scrubs water and nitric acid from the gaseous product stream. The amounts of water and nitric acid present in the gaseous product stream from the alkyl nitrite reactor thus are minimized. Conversely, the amount of alkyl nitrite, the preferred product, present in the liquid tails stream from the alkyl nitrite reactor similarly is minimized.

The amount of scrubbing agent required to provide the separation necessary to satisfy the above discussed requirements preferably is minimized since the use of excess scrubbing agent material is uneconomical.

Finally, Reaction I is highly exothermic, and it is necessary to remove heat from the alkyl nitrite reactor.

DESCRIPTION OF THE INVENTION

The present invention is directed to an alkyl nitrite manufacturing process, including a reaction vessel, which substantially meets the abovenoted performance criteria comprising:

(a) contacting nitric oxide, a lower alcohol and oxygen in a reaction zone under conditions wherein at least a portion of the nitric oxide, lower alcohol and oxygen react to form alkyl nitrite; said reaction zone comprising at least two sections, a reactor section and a rectification section;

(b) supplying a liquid scrubbing agent to an upper portion of the rectification section;

(c) withdrawing from the rectification section a gaseous reaction product steam comprising alkyl nitrite; and (d) withdrawing from a lower portion of the reactor section a liquid stream comprising scrubbing agent and water;

wherein the reactor section provides intimate vapor-liquid contact and cooling sufficient to enhance the conversion of nitric oxide to alkyl nitrite and wherein the rectification section provides sufficient vapor residence time to enhance conversion of oxygen, and sufficient rectification capabilities to reduce the amounts of water and nitric acid in the gaseous reaction product stream and the amount of alkyl nitrite in the liquid stream.

The present invention also is directed to a preferred reaction vessel for producing alkyl nitrite by contacting nitric oxide, a lower alcohol and oxygen. The reaction vessel comprises (a) a lower packed bed section, (b) an upper rectification section, (c) means for supplying a liquid scrubbing agent to the upper rectification section, (d) means for withdrawing a gaseous stream from the upper rectification section, and (e) means for withdrawing a liquid bottoms stream from the lower packed bed section. The lower packed bed section provides intimate vapor-liquid contact sufficient to enhance the conversion of nitric oxide to alkyl nitrite, and the upper rectification section provides sufficient vapor residence time to enhance conversion of oxygen and sufficient rectification capabilities to reduce the amounts of water and nitric acid in the gaseous reaction product stream and the amount of alkyl nitrite in the liquid bottoms stream.

Figure 1:
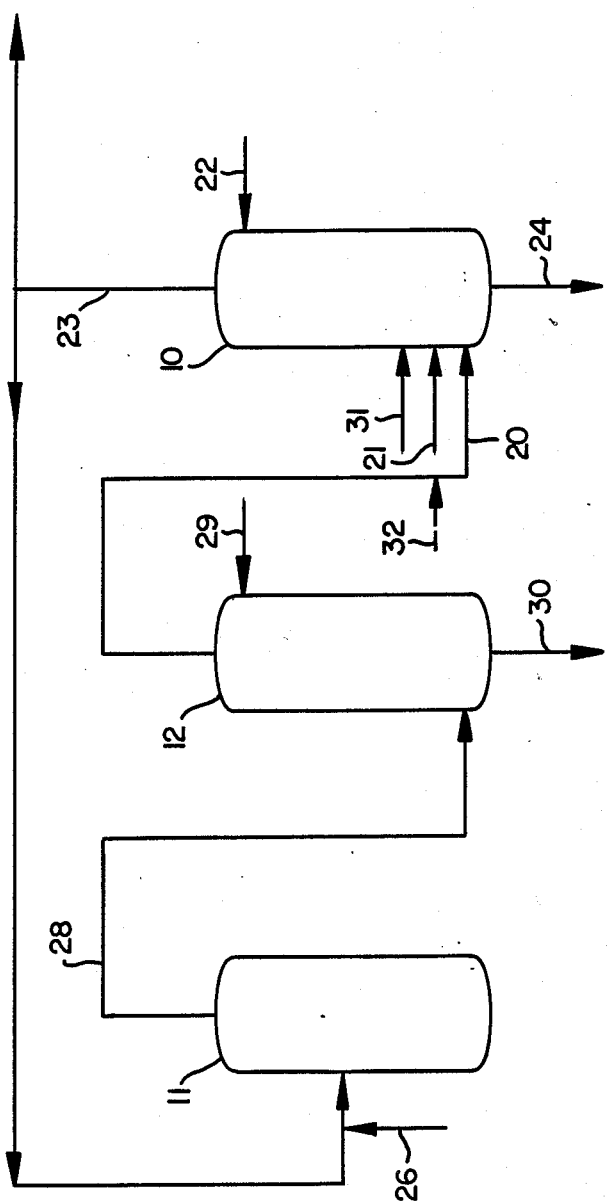
FIG. 1 is a flow chart of an alkyl nitrite-dialkyl oxalate production cycle.

The subject invention will be more easily understood with reference to the drawings. With reference first to FIG. 1, alkyl nitrite is produced in an alkyl nitrite reactor or alkyl nitrite regeneration column 10 (ANRC) by contacting nitric oxide and oxygen in the presence of a lower alcohol. In terms of the present invention, the lower alcohol includes $C_1$ to $C_4$ alcohols and preferably is selected from methanol, ethanol and mixtures thereof. Methanol is most preferred and thus the present invention will be described using methanol as the lower alcohol and methyl nitrite as the product.

Recycle nitric oxide, typically supplemented by makeup nitric oxide (solid line 31 and/or dotted line 32), is fed into the ANRC via line 20. Oxygen is supplied to the ANRC via line 21. The nitric oxide and oxygen streams preferably are supplied to the bottom of the ANRC. Liquid methanol is supplied to the top of the ANRC via line 22. Methanol advantageously serves as both a reactant and a scrubbing agent, as described more fully below.

As discussed above, the mole ratio of nitric oxide to oxygen in the ANRC preferably is greater than 4:1, typically ranging from slightly greater than 4:1 to 5:1. The actual flow rates of the various reactants into the ANRC can vary widely according to the ANRC design and size. The mole ratio of methanol to oxygen typically is in the range of from about 4:1 to about 12:1 or higher.

Methyl nitrite production preferably is carried out in a continuous manner at temperatures sufficiently high to maintain substantially all of the nitrogen oxide and methyl nitrite and only a portion of the methanol in the vapor state. The temperature in the ANRC typically is in the range of from about 10° to about 150° C., preferably from about 20° to about 130° C., and most preferably from about 30° to about 110° C.

The pressure within the ANRC is typically in the range of from about atmospheric to about 100 psia, preferably from about 20 to about 60 psia. Subatmospheric pressures, i.e., pressures less than 14.7 psia may be employed, if desired.

The gas hourly space velocity in the ANRC generally ranges from about 120 to about 36,000 $hr^{-1}$, preferably from about 1800 to about 36,000 $hr^{-1}$. Smaller or larger space velocities may be employed depending on the temperature, pressure, reactant molar ratios, gaseous diluent, and feed rate employed, so long as sufficient time for reaction is provided. In addition, the reactor design and geometry may have an effect on the preferred space velocity.

In general, the methyl nitrite formation process does not require the use of a catalyst. However, if desired, a suitable catalyst and/or catalyst support may be employed.

Mixing of the various feedstreams supplied to the reaction zone generally is achieved through the turbulent conditions present at their points of introduction, although mixing may be induced by other means as well.

The reactants supplied to the ANRC preferably are reacted according to Reaction (I):

(I) $2NO + 1/2 O_2 + 2ROH \rightarrow 2RONO + H_2O$ wherein R is methyl.

Unfortunately, some nitric oxide also is converted to nitric acid via the side reactions previously described. Thus, the material leaving the ANRC typically comprises nitric oxide, carbon monoxide, oxygen, and methyl nitrite together with a small amount of nitric acid, water and methanol. Substantially all of the nitric oxide, unreacted oxygen and methyl nitrite product exiting the ANRC are withdrawn from the top of the ANRC in the gaseous phase via line 23.

As mentioned above, a portion of the methanol supplied to the ANRC comprises a reactant, while a portion of it remains in the liquid phase as a scrubbing agent to scrub substantially all of nitric acid and water in the ANRC. Thus, substantially all of the nitric acid and water exiting the ANRC is removed in a liquid methanol-containing stream 24 which preferably is withdrawn from the bottom of the ANRC. Any water that does not exit the ANRC via the methanol-containing stream 24 is withdrawn from the top of the ANRC in the gaseous phase via line 23. A small portion of the methanol exiting the ANRC also is withdrawn from the top of the ANRC in the gaseous phase via line 23.

The liquid stream withdrawn from the ANRC via line 24 may be refined by distillation, extraction or the like to reduce its water and nitric acid content. The refined product then may be recycled as the lower alcohol, i.e., methanol.

In the integrated, alkyl nitrite-dialkyl oxalate process depicted in FIG. 1, at least a portion of the overhead vapor stream 23 from the ANRC, generally the major portion, is mixed with carbon monoxide supplied via line 26, preferably in the gaseous phase, and is supplied to a carbonylation reaction zone or oxalate reactor 11. Preferably all the materials entering oxalate reactor are substantially completely in the gaseous phase. In reactor 11, methyl nitrite is contacted with carbon monoxide in the presence of a catalyst to form dimethyl oxalate and nitric oxide according to Reaction (II):

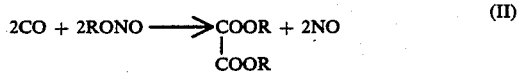

(II)

wherein R is the lower alkyl, e.g., methyl for the purposes of this description.

It may be preferable to carry out the carbonylation reaction in the presence of an inert gaseous diluent such as nitrogen or carbon dioxide. Carbon dioxide is preferred since it provides a higher heat capacity in comparison with nitrogen. Such gaseous diluent may comprise from about 0 to about 99 percent by volume of the gaseous feed. Typically, the concentration of gaseous diluent ranges from about 1 to about 90 percent by volume.

Suitable concentrations of carbon monoxide in the reaction mixture depend on the alkyl nitrite employed and its concentration, the catalyst used, the concentration of inert gaseous diluent, if diluent is employed, and the selected process conditions. In general, the higher the concentration of the alkyl nitrite, the more rapid the carbonylation reaction. The ratio of alkyl nitrite to carbon monoxide, by volume, typically is in the range of from about 0.05 to about 3.0, preferably from about 0.2 to about 1.0. A molar excess of carbon monoxide normally will be used.

The carbonylation reaction is carried out under conditions which essentially avoid the formation of a liquid phase in the carbonylation reaction zone 11. These conditions may vary depending upon the particular alkyl nitrite and its concentration. The carbonylation reaction generally is carried out at a temperature of from about 50° to about 200° C., preferably from about 75° to about 160° C., most preferably from about 120° to about 150° C. The carbonylation reaction pressure generally is from about atmospheric to about 220 psia, more preferably from about atmospheric to about 100 psia, and most preferably from about 15 psia to about 60 psia. Subatmospheric pressure may be employed, if desired. The gas hourly space velocity for the carbonylation reactor generally is greater than about 120 hr$^{-1}$, preferably from about 360 hr$^{-1}$ to about 72,000 hr$^{-1}$.

The carbonylation reaction zone 11 preferably does not contain water. While a very minor amount of water may be tolerated in the reaction zone, preferably substantially all of the water formed in the ANRC is removed prior to introducing the ANRC product stream into carbonylation reaction zone 11. The amount of water in the oxalate-forming reaction zone preferably is less than about 0.5 percent by volume.

The carbonylation reaction preferably is carried out in a continuous manner in a series of elongated tubular zones although alternative zone geometries and designs may be employed. The materials of construction should be such that they are inert to the reactants and products and are able to withstand reaction temperatures and pressures. Due to the exothermic nature of the carbonylation reaction, carbonylation reaction zone 11 may be fitted with internal or external heat exchange unit(s) to control temperature. Mixing in carbonylation reaction zone 11 generally is achieved through turbulence at the points of introduction for the various gaseous components. Other mixing mechanisms may be employed as well.

Carbonylation reaction zone 11 preferably is packed with a solid catalyst of the platinum group metal series. The preferred platinum group catalyst material is palladium. However, platinum, rhodium, ruthenium, and iridium also are useful. Furthermore, salts of these metals, such as nitrates, sulfates, phosphates, halides, acetates, oxalates, or benzoates may be used. These materials may be supported on a carrier such as active carbon, alumina, silica, silica-alumina, diatomaceous earth, pumice, magnesia, or zeolite. The amount of platinum group metal generally ranges from about 0.01 to about 10 percent by weight, preferably from about 0.2 to about 2 percent by weight, relative to the carrier. The solid catalyst generally may be supplied as a fixed bed or as a fluidized bed.

When a palladium catalyst is employed, it has been found that nitrous and nitric acids tend to accelerate the rate of deactivation of the catalyst. It is therefore preferable that substantially all of the nitrous acid produced in or supplied to the ANRC be consumed in the ANRC. Furthermore, since oxygen has similar deleterious effects on such catalysts, it is important to minimize the amount of unconsumed oxygen in the methyl nitrite product recovered from the ANRC.

Carbonylation reaction effluent 28, comprising dimethyl oxalate and nitric oxide is withdrawn from the carbonylation reaction zone 11 substantially completely in the vapor phase and preferably is supplied to an oxalate scrubber 12. A liquid scrubbing agent supplied to oxalate scrubber 12 via line 29 scrubs substantially all of the dimethyl oxalate from the carbonylation reaction effluent. Preferably, the scrubbing agent is the same material used as a scrubbing agent in the ANRC, i.e., methanol. A liquid bottoms stream 30 comprising the scrubbing agent and dimethyl oxalate, is withdrawn from the bottom of oxalate scrubber 12. Substantially all of the nitric oxide contained in the carbonylation reaction effluent 28, i.e., 95 percent or more, preferably 99 percent or more, is withdrawn from oxalate scrubber 12 in a gaseous overhead stream 20 and preferably is recycled to the ANRC, thereby completing the nitrite-oxalate cycle. Since some nitric oxide is consumed via side reactions in the ANRC, e.g., via the production of unwanted nitric acid, nitric oxide recovered from oxalate scrubber typically must be supplemented by makeup nitric oxide fed to the ANRC as a separate stream via line 31 or introduced into the recycle nitric oxide stream 20 via dotted line 32.

The ANRC in accordance with the present invention may conveniently comprise an elongated tubular reaction zone, preferably a column, although alternative zone geometries may be employed, which includes at least two sections, an upper rectification section and a lower reactor section. The lower reactor section preferably comprises a packed bed, while the upper rectification section preferably comprises a series of spaced distillation trays. The materials of construction should be such that they are inert to the reactants and products at reaction conditions and are able to withstand the temperatures and pressures encountered, stainless steel is suitable.

Nitric oxide and oxygen, preferably in the gaseous phase, are supplied to the lower reactor section of the ANRC, preferably below the packing. Consumption of oxygen occurs via the oxidation of nitric oxide (Reaction (1) discussed above):

(1) $2NO + O_2 \rightarrow 2NO_2$

This reaction is relatively slow and is believed to take place primarily in the gaseous phase proceeding in what may be referred to as vapor pockets within the ANRC. In the lower reactor section the vapor pockets principally consist of bubbles located in and generally moving upward through the continuous liquid phase in the packed bed. In the upper rectification or distillation section, the vapor pockets principally consist of the vapor space between trays, i.e., the space located above the liquid froth on one tray and below the tray above.

Two other reactions which take place in the vapor pockets are Reactions (2) and (6) discussed above:

(2) $NO + NO_2 \rightleftharpoons N_2O_3$ (6) $2NO_2 \rightleftharpoons N_2O_4$

Reaction of the $N_2O_3$ formed in Reaction (2) with methanol according to Reaction (3) is very fast and is believed to proceed in the liquid phase in what are referred to as liquid pockets within the ANRC. In the lower reactor section, liquid pockets primarily comprise the essentially continuous liquid phase located in and generally moving downwardly through the packed bed. In the upper rectification section, the liquid pockets primarily comprise the liquid froth on each distillation tray.

It is believed that the $N_2O_3$ formed in Reaction (2) also is capable of reacting with oxygen in the gaseous phase. Such further reaction of $N_2O_3$ produces a nitric acid precursor ($N_2O_5 + H_2O \rightarrow 2HNO_3$) and thus reduces the system's efficiency of converting nitric oxide to alkyl nitrite. Thus, to enhance the efficiency of the nitric oxide to alkyl nitrite conversion, it is preferred that $N_2O_3$ formed in Reaction (2) be forced to react relatively soon after formation with lower alcohol in accordance with Reaction (3). The reaction of $N_2O_3$ with lower alcohol is believed to occur predominantly where vapor and liquid come into contact.

Reaction (6) also reduces the system's efficiency of converting nitric oxide to alkyl nitrite and generally results in the formation of undesired nitric acid via Reactions (7) and (8). Reaction (6) is believed to occur in the gaseous phase. To minimize nitric acid formation, $NO_2$ formed by Reaction (1) preferably is caused to react soon after formation with NO according to Reaction (2) followed immediately by reaction in the liquid phase with lower alcohol, e.g., methanol to yield alkyl nitrite, i.e., methyl nitrite. It has been found that these considerations can be satisfied by a reactor section that provides intimate vapor-liquid contact and relatively low gas hold-up, such as a packed bed reactor. The use of a molar excess of NO relative to oxygen coupled with intimate contacting of the gas phase and the liquid alcohol phase in the absence of significant vapor pockets possible in a packed bed design, selectively promotes Reactions (1)-(4) and discourages Reactions (5)-(8). Thus, alkyl nitrite, the desired product, is formed instead of nitric acid. As an alternative to the packed bed design, the reactor section also might be provided as a spray section.

With that background, the design of a preferred ANRC vessel will now be described in more detail. The design requirements of the ANRC change significantly from the bottom to the top of the column. Nitric oxide and oxygen are fed to the bottom of the ANRC in a mole ratio such that the nitric oxide is present in a stoichiometric excess, i.e., the mole ratio of $NO:O_2$ is greater than 4:1. As long as a sufficient molar excess of nitric oxide is used, the oxygen concentration will be higher in the bottom of the ANRC relative to the rest of the ANRC where oxygen has been at least partially depleted by reaction with nitric oxide. In other words, provided an initial excess of oxygen is used, the nitric oxide/oxygen mole ratio generally will be lower in the bottom of the ANRC than anywhere else in the ANRC. As a result, the rate of Reaction (1) will, in general, be higher in the bottom of the ANRC than anywhere else in the ANRC. Because of the high rate of formation of $NO_2$, the rate of Reaction (2) also will be greater at the bottom of the ANRC relative to the rest of the column. In order to maximize the efficiency of the conversion of nitric oxide to alkyl nitrite, contact of $N_2O_3$ (formed via Reaction (2)) with lower alcohol, e.g., methanol should be maximized in the bottom section of the ANRC where the production of $N_2O_3$ is particularly rapid. This is effected by providing intimate contact of vapor and liquid in the bottom section. Packing, which generally provides an intimate contact of vapor and liquid, is therefore provided in the bottom section of the ANRC.

Some oxygen generally passes through the packed section unconsumed and enters the upper section. As noted above, essentially none of this oxygen is desired in the methyl nitrite product which is delivered to the oxalate reactor. In order to maximize the oxygen consumption within the ANRC and achieve this goal, it is therefore desirable to provide a means for consuming substantially all of the oxygen that enters the upper section of the ANRC. In general, the concentration of oxygen becomes progressively lower the higher in the column the concentration is measured. Because of this the rate of Reaction (1) is relatively low in the upper section of the column and, for similar reasons, the rates of Reactions (2) and (6) also will be low. As such, relatively extensive vapor phase residence time should be provided with relatively low vapor-liquid contact necessary in the upper rectification section of the column to complete the consumption of oxygen without seriously adversely affecting the overall efficiency of the conversion of nitric oxide to methyl nitrite in the ANRC. By providing relatively long vapor phase residence time in the upper rectification section of the ANRC, substantially all of the oxygen, typically 99 percent or more, entering the upper rectification section can be consumed. Sufficient vapor phase residence time readily can be provided in the upper rectification section which comprises a trayed distillation section.

For reasons discussed in the Background of the Invention section, the amount of water and nitric acid contained in the vapor product of the ANRC and the amount of methyl nitrite in the liquid bottoms stream of the ANRC preferably are minimized. Temperatures and pressures are maintained within the ANRC such that adequate separation of the compounds is effected within the ANRC. To best achieve this result, a scrubbing agent is introduced into the upper portion of the rectification section, preferably above the top tray, to assist the separation. Preferably, methanol supplied as a reactant also serves as the scrubbing agent. In general, the more scrubbing agent employed, the better the rectification. The amount of scrubbing agent required to obtain a certain separation can be reduced by providing more trays in the ANRC. There is thus an economic optimization between using greater amounts of scrubbing agent and providing more trays in the ANRC.

By providing adequate vapor phase residence time, substantially all of the oxygen fed to the ANRC, i.e., 99 percent or more, and substantially all of the oxides of nitrogen other than nitric oxide, i.e., 99 percent or more, will be consumed in the ANRC.

Finally, as discussed in the Background of the Invention section, the heat of reaction must be removed efficiently from the ANRC. In general, greater than about 90 percent, and typically 95 percent or more, of the total heat generated within the ANRC occurs in the lower packed bed section. Heat removal is preferably accomplished by recirculating a side stream of the liquid from the lower reactor section through a heat exchanger.

Heat removal also may be desirable in the lower portion of the upper rectification section of the ANRC. This also may be accomplished by providing additional heat exchange means, similar to that described above. For example, liquid may be withdrawn from one tray, passed through a cooler, and returned to the ANRC at a higher tray.

Figure 2:
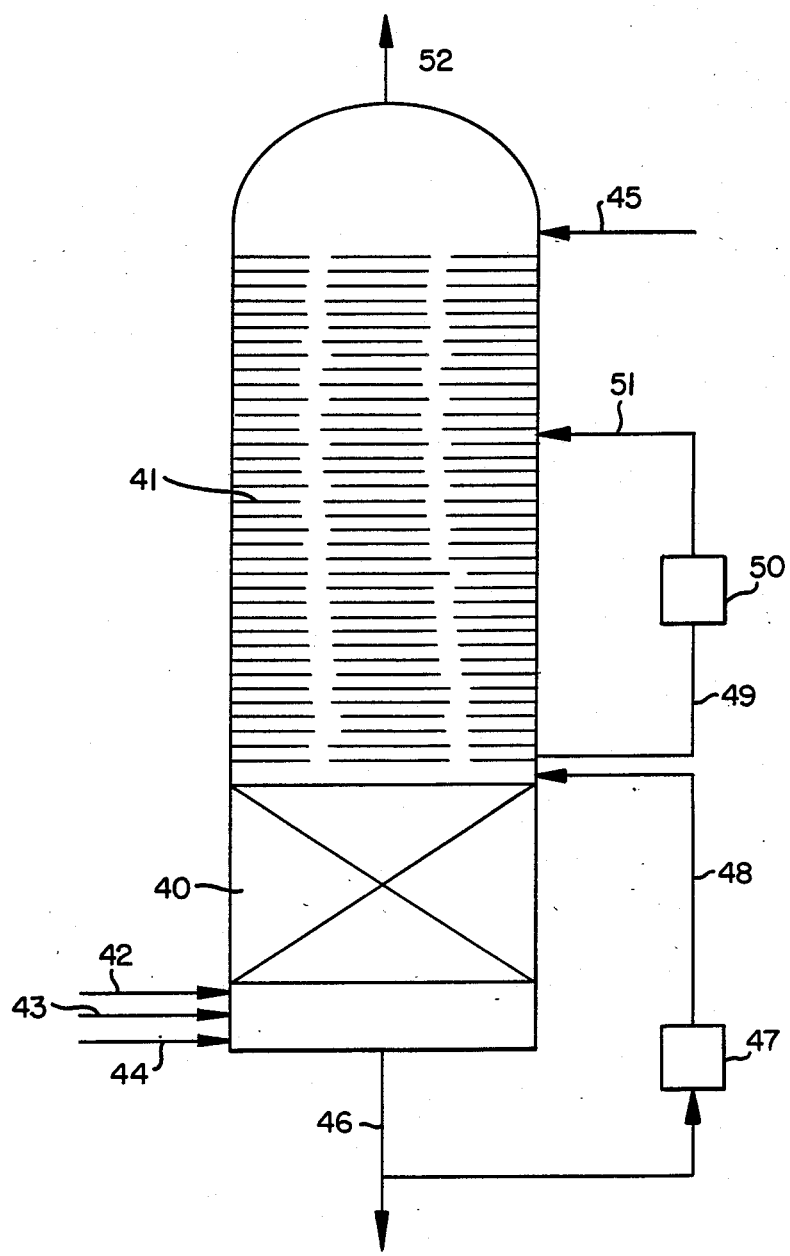
FIG. 2 is a schematic drawing of a preferred alkyl nitrite reactor in accordance with the present invention.

An illustration of a preferred ANRC in accordance with the present invention is depicted in FIG. 2. Referring to FIG. 2, a lower packed bed reactor section 40 may comprise about 20 vertical feet of packing. The upper rectification section 41 comprises about 36 trays with a tray spacing of about 2 feet. Packing also might be employed in the upper rectification section 41, although there might be a problem with adequate liquid distribution needed to ensure efficient rectification. Even without such a problem, however, the added cost of packing is not justified since a sizeable gas hold-up is not problematic, and actually desired to complete oxygen consumption. Thus, trays are preferred.

In the preferred embodiment, the lower reactor section and the upper rectification section are provided in a single, subdivided column shell. In any event, means are provided to pass gas/vapor from the packed bed reactor section directly into the upper rectification section and to conduct liquid from the rectification directly into the packed bed reactor section.

Recycle nitric oxide, makeup nitric oxide and oxygen are fed to the bottom of the ANRC, in the lower portion of the reactor section below the packing, via lines 42, 43 and 44, respectively. Liquid methanol is supplied via line 45 to a location above the uppermost tray in the upper portion of the rectification section. Liquid stream 46, comprising methanol, nitric acid and water, is withdrawn from the lower portion of the reactor section below the packing. A portion of liquid stream 46 is cooled in heat exchanger 47 and returned to the ANRC at a location just above the packed section via line 48. In addition, liquid stream 49 withdrawn from the bottom tray in the ANRC, is passed through a second heat exchanger 50, and returned to the ANRC on about the 23rd tray from the bottom of the upper rectification section via line 51. Overhead stream 52, comprising product methyl nitrite, is withdrawn from the top of the ANRC.

In accordance with the subject invention, methyl nitrite can be produced in an efficient manner with (1) substantially complete conversion of oxygen, i.e., at least 95 percent, preferably 99 percent or higher, most preferably 99.5 percent or higher, (2) substantially complete conversion of higher nitrogen oxides, and (3) a high efficiency of conversion of nitric oxide to methyl nitrite, i.e., at least 95 percent, preferably 99 percent or higher. Additionally, substantially all the nitric acid and water formed in the ANRC are removed via a liquid tails stream while the gaseous overhead stream comprising methyl nitrite is substantially free of these materials.

The invention will be better understood by reference to the following example, which is offered by way of illustration and not limitation.

EXAMPLE

This example presents the results of a computer simulation study of a preferred ANRC designed in accordance with the present invention. The ANRC was patterned after the FIG. 2 design and included a lower packed bed reactor section having 20 vertical feet of packing, and an upper rectification section (69 feet high) that contained eight theoretical equilibrium separation stages. Actually, the lower 43 feet of the upper rectification section contributed only a single equilibrium stage to the rectification since a side cooling loop, as shown in FIG. 2, bracketed this portion of the ANRC.

In this simulation, the ANRC was operated at approximately 5 atmospheres pressure and 50° C. NO and $O_2$ were fed to the bottom of the packed bed section in a mol ratio of about 5:1, while substantially pure methanol was introduced into the top of the rectification section. With this arrangement over 99% of the NO fed to the ANRC was converted to methyl nitrite producing an overhead product containing less than 10 ppm of $HNO_3$ and only about 20 ppm of water and 50 ppm of oxygen. This represents an oxygen conversion in the ANRC of about 99.7%. The liquid stream withdrawn from the lower portion of the reactor section contained about 13 mol percent methanol, about 1 mol percent $HNO_3$ and only about 0.1 mol percent methyl nitrite with the balance being water.

Although certain embodiments of the invention have been described in detail, it will be appreciated that other embodiments are contemplated along with modifications of the disclosed features, as being within the scope of the invention, which is defined in the appended claims.

I claim:

1. A process for producing alkyl nitrite comprising:
   (a) contacting nitric oxide, a lower alcohol and oxygen in a reaction zone under conditions wherein at least a portion of said nitric oxide, lower alcohol and oxygen react to form alkyl nitrite, said reaction zone comprising at least two sections, a lower reactor packed bed section and an upper rectification section containing spaced distillation trays;

(b) supplying a liquid scrubbing agent to an upper portion of said rectification section;

(c) withdrawing from said rectification section a gaseous reaction product stream comprising alkyl nitrite;

(d) withdrawing from said reactor section a liquid stream comprising scrubbing agent and water;

wherein said reactor section provides intimate vapor-liquid contact and cooling sufficient to enhance the conversion of nitric oxide to alkyl nitrite and said rectification section provides sufficient vapor residence time to enhance conversion of oxygen and sufficient rectification capabilities to reduce the amounts of water and nitric acid in the gaseous reaction product stream and the amount of alkyl nitrite in the liquid stream.

2. The process of claim 1 wherein said alkyl nitrite is methyl nitrite, said lower alcohol is methanol and said liquid scrubbing agent is methanol.

3. The process of claim 1 wherein said alkyl nitrite is ethyl nitrite, said lower alcohol is ethanol and said liquid scrubbing agent is ethanol.

4. The process of claim 1 wherein heat is removed from said reaction zone by withdrawing a liquid side stream from said reactor section, cooling said liquid side stream and returning said liquid side stream to said reaction zone.

5. The process of claim 4 wherein said rectification section comprises a series of spaced trays and additional heat is removed from said reaction zone by withdrawing a second liquid side stream from a bottom tray in said rectification section, cooling said second liquid side stream and returning it to said rectification section at a higher location in said rectification section than said bottom tray.

6. The process of claim 2 wherein the conversion of oxygen in said reaction vessel is at least 95 percent and the conversion of nitric oxide to methyl nitrite is at least 95 percent.

7. The process of claim 2 wherein the conversion of oxygen in said reaction vessel is 99 percent or higher and the conversion of nitric oxide to methyl nitrite is 99 percent or higher.

8. A process for the production of methyl nitrite comprising contacting nitric oxide, methanol and oxygen in a reaction zone, said reaction zone comprising at least two sections, a lower packed bed section and an upper rectification section containing spaced distillation trays wherein:

(1) oxygen conversion is 99 percent or higher, and (2) nitric oxide efficiency to alkyl nitrite is 99 percent or higher.

* * * * *